(12) United States Patent
Nordbryhn et al.

(10) Patent No.: US 6,433,338 B1
(45) Date of Patent: Aug. 13, 2002

(54) METHOD AND DEVICE FOR IDENTIFICATION OF A TYPE OF MATERIAL IN AN OBJECT AND UTILIZATION THEREFOR

(75) Inventors: Andreas Nordbryhn, Oslo; Alain Ferber, Haslum; Håkon Sagberg, Oslo, all of (NO)

(73) Assignee: Tomra Systems ASA, Asker (NO)

( * ) Notice: Subject to any disclaimer, the term of this patent is extended or adjusted under 35 U.S.C. 154(b) by 0 days.

(21) Appl. No.: 09/601,286

(22) PCT Filed: Feb. 8, 1999

(86) PCT No.: PCT/NO99/00039

§ 371 (c)(1),
(2), (4) Date: Sep. 22, 2000

(87) PCT Pub. No.: WO99/40414

PCT Pub. Date: Aug. 12, 1991

(30) Foreign Application Priority Data

Feb. 9, 1998 (NO) ............................................. 19989545

(51) Int. Cl.⁷ .............................................. G01N 21/35
(52) U.S. Cl. .............................. 250/339.12; 250/339.11
(58) Field of Search ....................... 250/339.12, 339.11, 250/341.8; 209/3.1; 194/212

(56) References Cited

U.S. PATENT DOCUMENTS

| | | | |
|---|---|---|---|
| 786,736 A | | 4/1905 | Dornberger et al. |
| 4,719,351 A | * | 1/1988 | Schoeller et al. ........... 250/339 |
| 5,067,616 A | * | 11/1991 | Plester et al. ................. 209/3.1 |
| 5,318,172 A | * | 6/1994 | Kenny et al. ................ 209/524 |
| 5,449,677 A | | 9/1995 | Maryanoff et al. |
| 5,512,752 A | * | 4/1996 | Aikawa et al. ......... 250/339.12 |
| 5,695,039 A | * | 12/1997 | Driscoll et al. .............. 194/212 |

FOREIGN PATENT DOCUMENTS

| | | |
|---|---|---|
| DE | 3416594 A1 | 5/1984 |
| DE | 43 40 795 A1 | 3/1995 |
| DE | 195 43 134 A1 | 11/1995 |
| DE | 196 01 923 C1 | 7/1997 |
| GB | 2 250 814 A | 2/1991 |

* cited by examiner

Primary Examiner—Constantine Hannaher
Assistant Examiner—Otilia Gabor
(74) Attorney, Agent, or Firm—Rodman & Rodman (57) ABSTRACT

A method and apparatus for identifying a material type in an article, such as wholly or partly transparent bottle of plastic or glass, including, with the aid of a detector station, irradiating the article with rays from an infrared radiation source, detecting rays which have passed through the article non-absorbed, and then carrying out a correlation analysis of such detected rays. The article is made to pass through the detector station in a continuous or discontinuous movement. The rays from the radiation source are successively filtered by the filters consisting of wholly or partly transparent materials which have different spectral characteristics. The rays filtered by the filters and non-absorbed by the article are intercepted in order to form a sequence of measured values representing characteristic transmission signatures of the article. A correlation analysis of the signatures is carried out in relation to statistical models in order to determine the material type of the article.

35 Claims, 7 Drawing Sheets

METHOD AND DEVICE FOR IDENTIFICATION OF A TYPE OF MATERIAL IN AN OBJECT AND UTILIZATION THEREFOR

The present invention relates to a method and apparatus for identifying a material type in an article, such as a wholly or partly transparent bottle of plastic or glass, comprising, with the aid of a detector station, irradiating the article with rays from an infrared radiation source, detecting rays which have passed through the article non-absorbed, and then carrying out a correlation analysis of such detected rays, as is set forth in the preamble of the enclosed patent claims.

The invention also relates to a use of the method and apparatus in a reverse vending machine for identifying and sorting bottles of different types of material.

Identification of different material types, and especially types of plastics, is a problem area of growing importance, partly as a result of materials recycling becoming a progressively higher priority, from both a private financial and a socioeconomic point of view. If collection programmes for used materials are to be of maximum profitability, it is essential to ensure that the materials are as pure as possible as early as possible in the collection and handling chain. Pure materials have a value as raw materials for re-use, and there is a well-developed market and industry which handle such materials. If the materials are not pure, payment must often be made for their disposal.

A number of methods for identifying different types of plastics are previously known. A reliable method, which is frequently used, is spectroscopy in the infrared range. All known instruments for such spectroscopic identification of plastics are costly, as both the wave-length selecting elements (e.g., filters or gratings) and also the infrared sources and detectors are expensive.

As further illustration of the prior art in connection with, inter alia, the use of spectroscopy and infrared light, reference is made to U.S. Pat. Nos. 5,512,752, 4,719,351, 5,206,510, German patent publications DE 19601923, 19543134 and 4340795, and the Japanese patent applications JP-A-9138194, 6288913 and 6210632.

A number of other methods and equipment for the detection of plastics have also been developed which are somewhat cheaper than spectroscopic methods and equipment, but where the result of the detection is less reliable. Examples of such known equipment are the triboelectric detector and the optical double refraction detector.

Furthermore, the use of so-called correlation spectroscopy is known in connection with the measurement of gases, both for the detection of gases and concentration measurement. The gas to be analysed is used as a filter.

The object of the present invention is to use a similar technique for the detection of plastic materials. Absorption spectra of solid substances such as plastics are very different from the absorption spectra of gases. Whilst gases have very many, very fine lines in the spectrum, plastic materials have fewer and broader lines, so that as a rule the spectra of different materials have more or less overlapping lines. In such a situation, more information is obtained about the material to be identified by measuring the degree of spectral overlapping with a number of different plastic materials.

The method mentioned above is characterised, according to the invention, by causing the article to pass through the detector station in a continuous or discontinuous movement;

causing the rays from the radiation source to be filtered successively by filters consisting of wholly or partly transparent materials having different spectral characteristics;

intercepting the rays filtered by the filter and non-absorbed by the article to form a sequence of measured values representing characteristic transmission signatures of the article; and carrying out a correlation analysis of the signatures in relation to statistical models in order to determine the material type of the article.

Similarly, the apparatus mentioned above is characterised by a conveyor controlled by a means to cause the article to move continuously or discontinuously and to pass through the detector station;

a device in the detector station provided with a plurality of filters consisting of wholly or partly transparent materials having mutually different spectral characteristics to effect successive and different filtration of the rays from the radiation source;

a means arranged to intercept the rays filtered by the filter and non-absorbed by the article and form a sequence of measured values representing characteristic transmission signatures; and an analyser, e.g., a microprocessor, which is adapted to carry out a correlation analysis of the signatures in relation to statistical models in order to determine the material type of the article.

Here, statistical models should be understood to mean pre-established reference values, so-called calibration values which are related to signatures of certain types of material.

Additional embodiments of the method and the apparatus are set forth in the attached patent claims and in the description below with reference to the attached drawings.

As mentioned above, an advantageous application of the method and apparatus would be to use them in a reverse vending machine to identify and sort bottles of different material types.

The invention will now be described in more detail with reference to the attached drawings which show embodiments that do not define the limits of the invention.

Figures 1, 4:
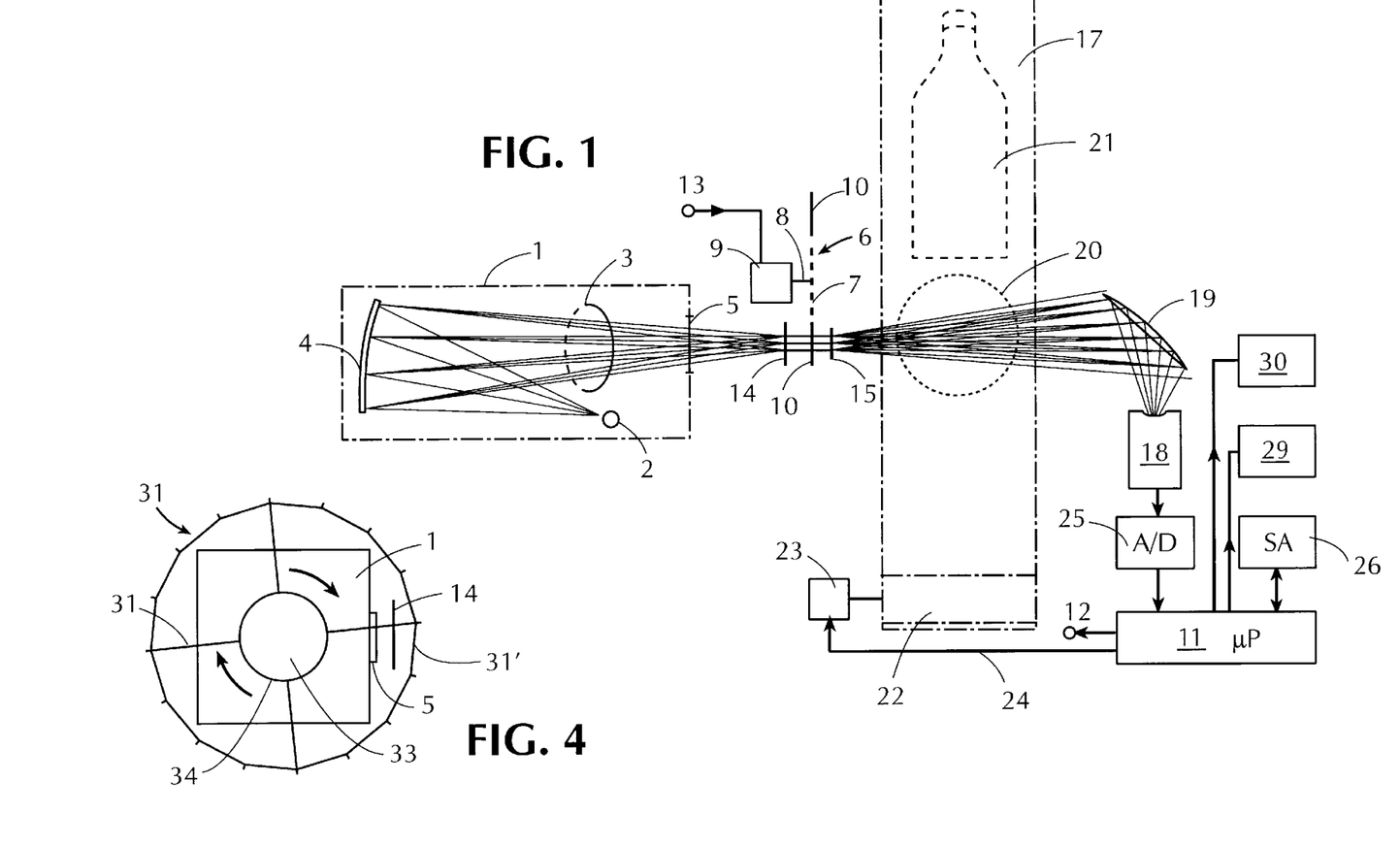
FIG. 1 illustrates the principle of the apparatus according to the present invention.
FIG. 4 is a top view of an alternative embodiment of a filter device and its location in a detector station.

The apparatus according to the invention has a detector station, including an infrared radiation source 1 which has a hot element 2 that emits infrared rays 3, optionally via a mirror 4. The radiation source 1 has an illuminator aperture 5 and the infrared beam is guided towards a filter device 6, preferably consisting of a rotatable, round or polygonal disc 7 which via a rotation shaft 8 is caused to rotate by a motor 9 which via cable connection 12, 13 is supplied with electric drive current under the control of a microprocessor 11. The light filter device 6 is provided with a plurality of different light filters 10. In a preferred test version, as shown in FIG. 3, the chosen number of light filters is ten.

In order to provide a wavelength limitation, it would be advantageous to provide an envelope filter 14 between the illuminator aperture 5 of the radiation source 1 and the filter device 6. Furthermore, it is also advantageous to position a diaphragm 15 in the path of the light beam. The filters 10 provided on the filter device in the form of a wheel or a rotating disc consist at least in part of a number of light-transparent pieces of different types of plastic material, e.g., selected from the material group consisting of polyethylene terephthalate, polyethylene naphthalate, polyvinyl chloride, polypropylene, polyethylene, polystyrene, acrylonitrile-butadiene-styrene copolymer, polymethyl methacrylate, polyamide, polyurethane, polysulphonate and polycarbonate. In addition, at least one of the filters may optionally be of glass, e.g., Pyrex® glass.

Although FIG. 1 shows the order of the envelope filter 14, the filter device 6 and the diaphragm 15 preferred at present, it should be appreciated that their position relative to one another may de different. Similarly, it is conceivable that one or more of these components may, e.g., be positioned on the opposite side of the conveyor 17. Furthermore, it is possible that, e.g., the diaphragm 15 and the envelope filter 14 may made in the form of a single unit, or that the filter device 6 and the diaphragm 15 may be combined into one unit.

Figure 3:
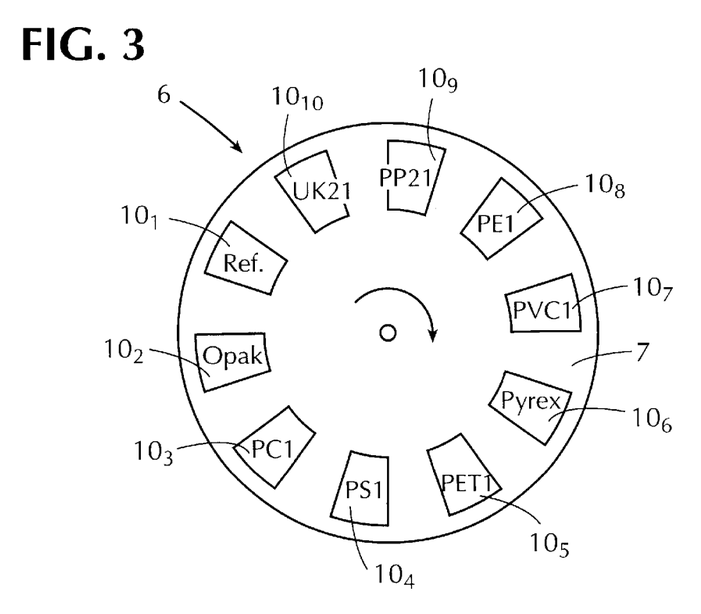
FIG. 3 shows a filter device for use with the apparatus according to the invention.

In FIG. 3 the filters 10 used in the filter device are indicated by the references $10_n$ and where in the chosen example n=1 . . . 10. However, it will be appreciated that more or fewer filters are possible within the scope of the invention, as will also be referred to in connection with FIG. 4.

Figure 2:
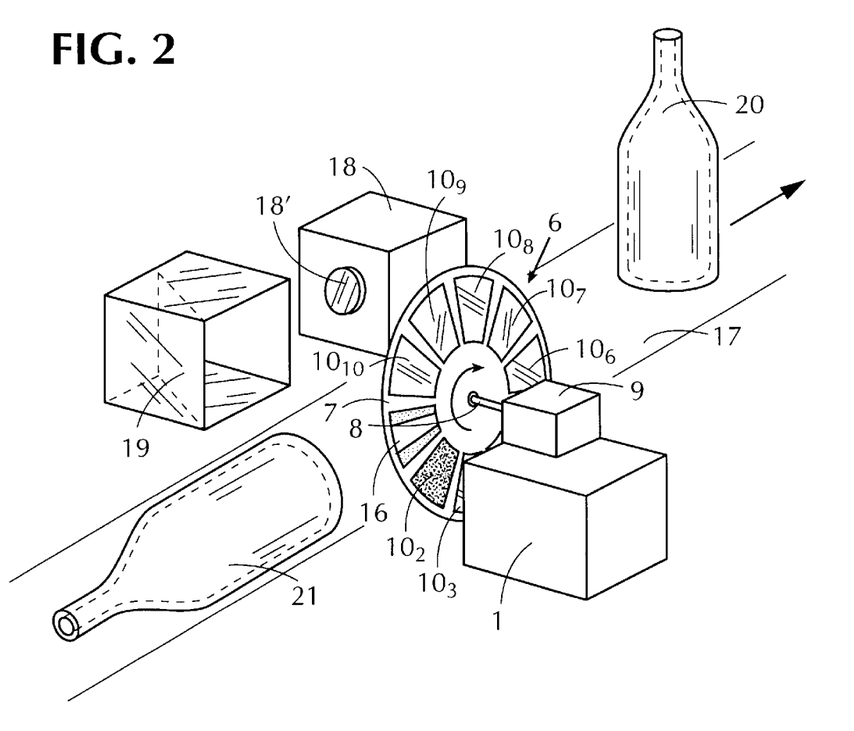
FIG. 2 is a perspective view of part of the apparatus shown in FIG. 1.

Of the filters shown in FIG. 3, the filter $10_1$ forms a reference filter which preferably is made of a spectrally uniform or material-free diaphragm 16 (see FIG. 2). The filter $10_2$ is of an opaque material, e.g., completely black, thus preventing the passage of light rays therethrough. Due to its area-limiting light ray penetrability through the diaphragm or aperture 16, the filter $10_1$ produces a signal peak reference value in the sequences of measured values. The light ray impenetrability of the filter $10_2$ will create a trough reference value in the sequence of measured values.

In the test installation, the other filters $10_3$, $10_4$, $10_5$, $10_6$, $10_7$, $10_8$, $10_9$ and $10_{10}$ were chosen from materials consisting respectively of polycarbonate (PC), polystyrene (PS), polyethylene terephthalate (PET), glass (Pyrex® glass), polyvinyl chloride (PVC), polyethylene (PE), polypropylene (PP) and polyethylene with an applied film, here designated UK21. After the light rays have passed the diaphragm 15, they will, possibly somewhat more concentrated (collimated) than indicated in FIG. 1, pass over a conveyor 17 and then to a detector 18 with a lens 18', optionally via a focusing mirror 19.

In those cases where the article to be detected is a bottle, the bottle may either be transported in an upright position as indicated by means of the reference numeral 20, or in a horizontal position as indicated by means of the reference numeral 21. The conveyor 17 is driven via driving roller 22 from a motor 23, and the operation of the motor can be controlled from the microprocessor 11 via a control cable 24. If it is desirable to cause the article to be detected to stop in the detection zone or optionally to pass through at a reduced speed, this can be controlled from the microprocessor 11 via the output 24 to the motor 23. The conveyor 17 may be of any type. If the bottle is transported in a horizontal position, as indicated by means of the reference numeral 21, the conveyor may, for instance, consist of spaced continuous cords or wires.

The conveyor 17 may move either continuously or discontinuously. The conveyor may also conceivably be a rotating plate which is driven continuously or discontinuously.

It is also conceivable that the bottles could arrive at the detection zone (i.e., in the light beam 3) at such intervals that the bottle for a brief instant can be held motionless there. If the conveyor 17, for instance, is not a belt-based conveyor, but a tube or chute, the bottle could conceivably be held motionless for a brief instant in the detection zone, so that determination of the material type of the bottle may easily be made in that the light rays pass into the transport channel or chute through an opening therein and pass out through an opening on the other side of the chute.

By causing the filter device 6 with its disc 7 containing the filters 10 to rotate, the filters will in turn come into the light transmission path of the light rays 3. A sequence of signal pulses of varying intensity, one for each of the filters used, will thus be emitted from the detector 18. The signal intensity of the measured values in the sequence will be dependent upon the material type in the article under examination, and will moreover be highly characteristic for each type of material, especially when using plastic materials typical for the article.

Articles examined in this way will, together with the successive filters, bring about a sequence of characteristic transmission signatures for each individual article.

The present invention could advantageously be used for identifying a number of typical plastic materials, such as polyethylene terephthalate (PET), polyethylene naphthalate (PEN), polyvinyl chloride (PVC), polyethylene (PE), polypropylene (PP), polycarbonate (PC), polystyrene (PS), acrylonitrile-butadiene-styrene copolymer (ABS), polymethyl methacrylate (PMMA), polyamide (PA), polyurethane (PUR), polysulphonate (PSU) etc. The same materials as those which are to be identified are used as filter materials for the filters 10 (see the filters $10_3$–$10_{10}$ in FIG. 3). The selectivity attainable will be further increased, the more filters and filter materials that are used. A filter device 6 such as that shown in FIGS. 1, 2 and 3, will potentially be very inexpensive to manufacture, as the plastic materials used as filters are very inexpensive, and at the same time they allow the passage of radiation in a wide wavelength range. This makes total transmitted radiation high, which in turn allows use of detectors 18 of such types that are inexpensive, for example, pyroelectric detectors, thermoelectric detectors or uncooled photoconductors such as PbS and PbSe. It will be possible to optimise selectivity of the method and apparatus according to the invention by limiting the spectral range used to a wavelength range wherein the materials used have different characteristic spectral features or transmission signatures. A limitation of this kind may be made using band pass filters, and an example of such a filter is indicated by the reference numeral 14 in FIG. 1. The wavelength range may, e.g., extend from about 3 micrometers to about 4 micrometers, preferably from 2 to 2.5 micrometers or alternatively from about 1.6 to 1.8 micrometers.

Of course, other wavelength ranges are also conceivable in connection with possible other plastic materials which are to be detected.

Figure 5:
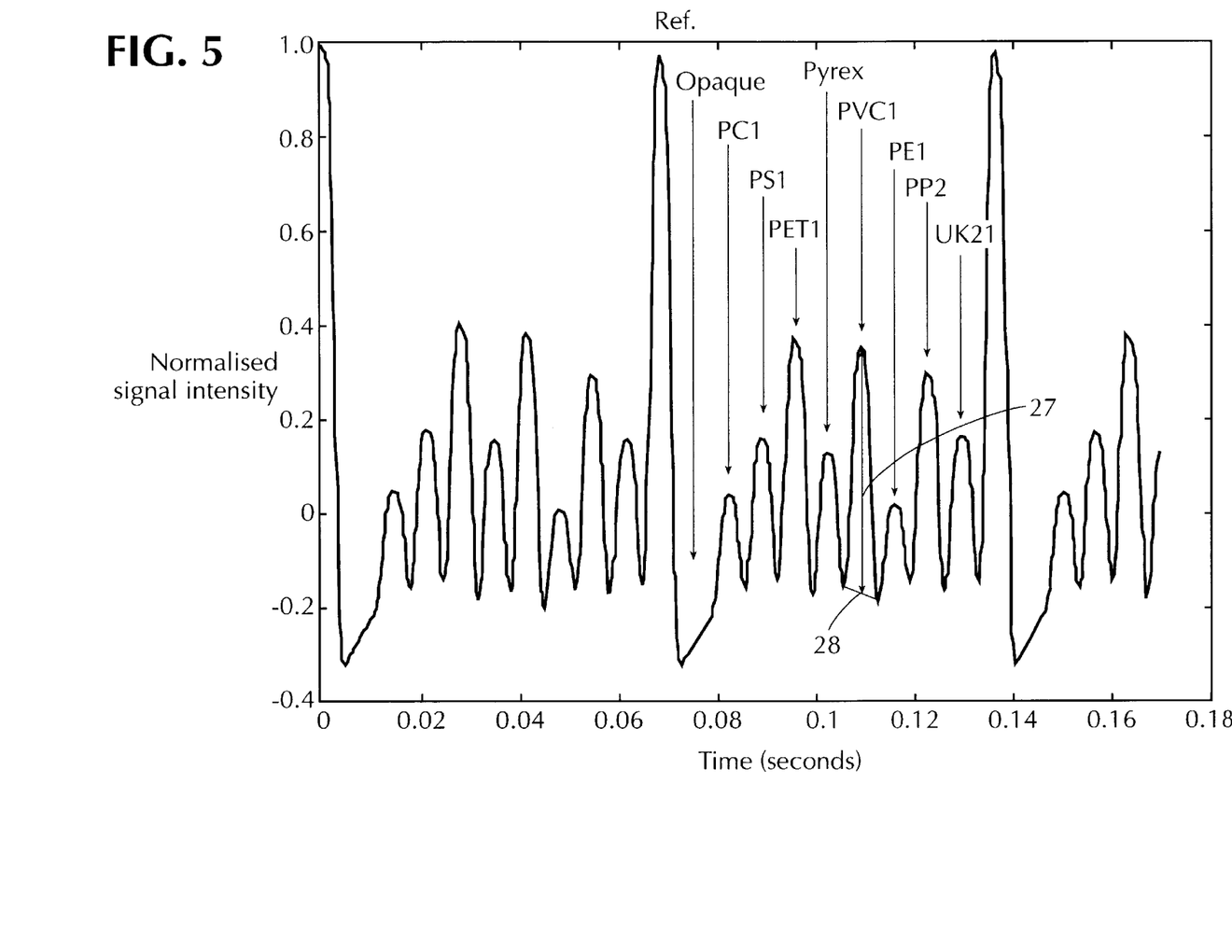
FIG. 5 shows a measured light signal after preliminary treatment in order to give transmission signatures as a function of time for a number of different materials.

The repeated sequence of signal pulses emitted from the detector 18 can be seen from FIG. 5 as a typical example.

These signal pulses are passed to an analog/digital converter 25, from where signals are passed to the microprocessor 11. As shown in FIG. 5, the reference filter 10, will provide a distinct reference pulse designated "Ref" on FIG. 5. The opaque filter material 102 will produce the signal valley which is indicated by the reference Opaque. The signal spectrum thus contains a reference signal peak caused by the area-limited, unfiltered light, and the reference signal trough that is due to a blocking of the light rays. The microprocessor 11 will analyse successively each of the other signal peaks in the sequence of measured values, e.g., the signal peak 27 (FIG. 5) relative to a mean value 28 of two adjacent signal valley.

On the basis of the measurements taken, it will be possible to compute a light transmission value for an article based on the level value 26 of a respective signal peak minus the said mean value. The said values may optionally be determined on the basis of a normalised signal intensity, as can also be seen from FIG. 5. As FIG. 5 shows, in a test installation, it was possible to carry out a scanning cycle in the course of about 70 milliseconds. The microprocessor II operates so that on the computation of the light transmission values it collects the sequence of the computed light transmission values from a signal cycle in a vector consisting of n elements, wherein n is equal to the number of filters, and compares this with corresponding measured values for a subsequent signal sequence or scanning sequence.

The microprocessor 11 is capable of computing the average value of two successive signal sequence values and deriving with the aid of a calibration or identification operation, e.g., PLS (Partial Least Squares) discriminant analysis, a unique characteristic of the material type of which the article is made. This calibration and identification operation includes use of a calibration and identification algorithm.

Although the design of the filter device shown and described in connection with FIGS. 1–3 may be typically like that shown in FIGS. 2 and 3, it is quite conceivable that the filters 10 arranged on the filter device 6 may be positioned closer together.

As an alternative, it is possible that the filter device may have the appearance of a drum-like structure, e.g., produced using extruded aluminium or plastic. The drum 31, in the proposed exemplary embodiment, may have a vertical or horizontal rotation shaft, depending upon the design and position of the radiation source 1. The drum 31 is supported by arms 32 which are secured to the rotation shaft 34 of the driving motor 33. The said filters can be placed in open sections 31' in the wall of the drum. By dividing the drum wall up as shown in FIG. 4, it will be possible to position a total of 16 filters. However, it will be appreciated immediately that it will be possible to position a larger or smaller number of filters on the drum, depending upon the number of filter openings that are provided. The drum may be circular in cross-section, or optionally have a polygonal cross-section.

It is also conceivable that the drum 31 may be positioned on the detector side of the conveyor 17, e.g., rotating about the detector 18 instead of about the radiation source 1.

The motor 33 which turns the drum 31 may, e.g., be a DC motor like the motor 9 in FIG. 1

When an article, such as a bottle 20 or 21, is placed in the light path between the radiation source 1 and the detector 18, for each revolution of the filter device, an irradiation is carried out with n different spectral characteristics, depending upon the number of filters used. The transmitted radiation is measured continuously by the detector. A signal amplifier can be installed in the detector and through the analysis of the transmission values it will be possible to make a very reliable classification of the different types of plastic. In a rudimentary test of the present invention, when testing a limited number of articles, an accuracy of 80% was attained, whilst 16% could not be classified and 4% were incorrectly classified. However, it should be understood that a refining of the calibration or identification algorithm and the equipment used will increase the accuracy of the measurements.

Figure 7:
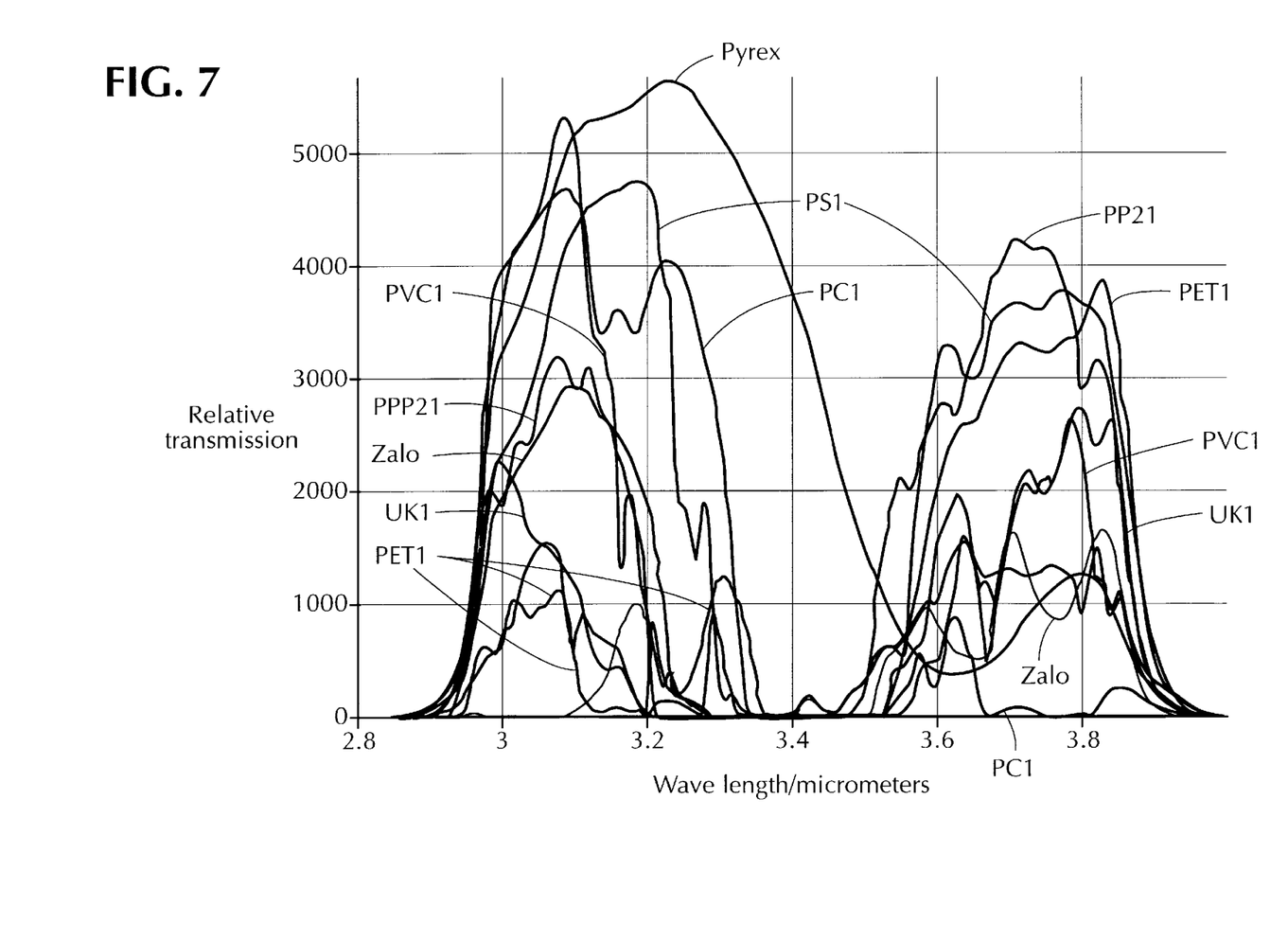
FIG. 7 shows test result of the spectral transmission of selected filter materials, multiplied by the transmission of an envelope filter.

The filters used in the filter device 6 consist typically of bits of sectors of a circle. In addition to the various polymers, Pyrex® glass was found to be suitable as a filter material. The spectral transmission of the filter materials multiplied by the transmission of the envelope filter 14 can be seen in more detail in FIG. 7. However, the filter materials shown in this figure must not be perceived as in any way defining the limits of the application of the invention.

Figure 8:
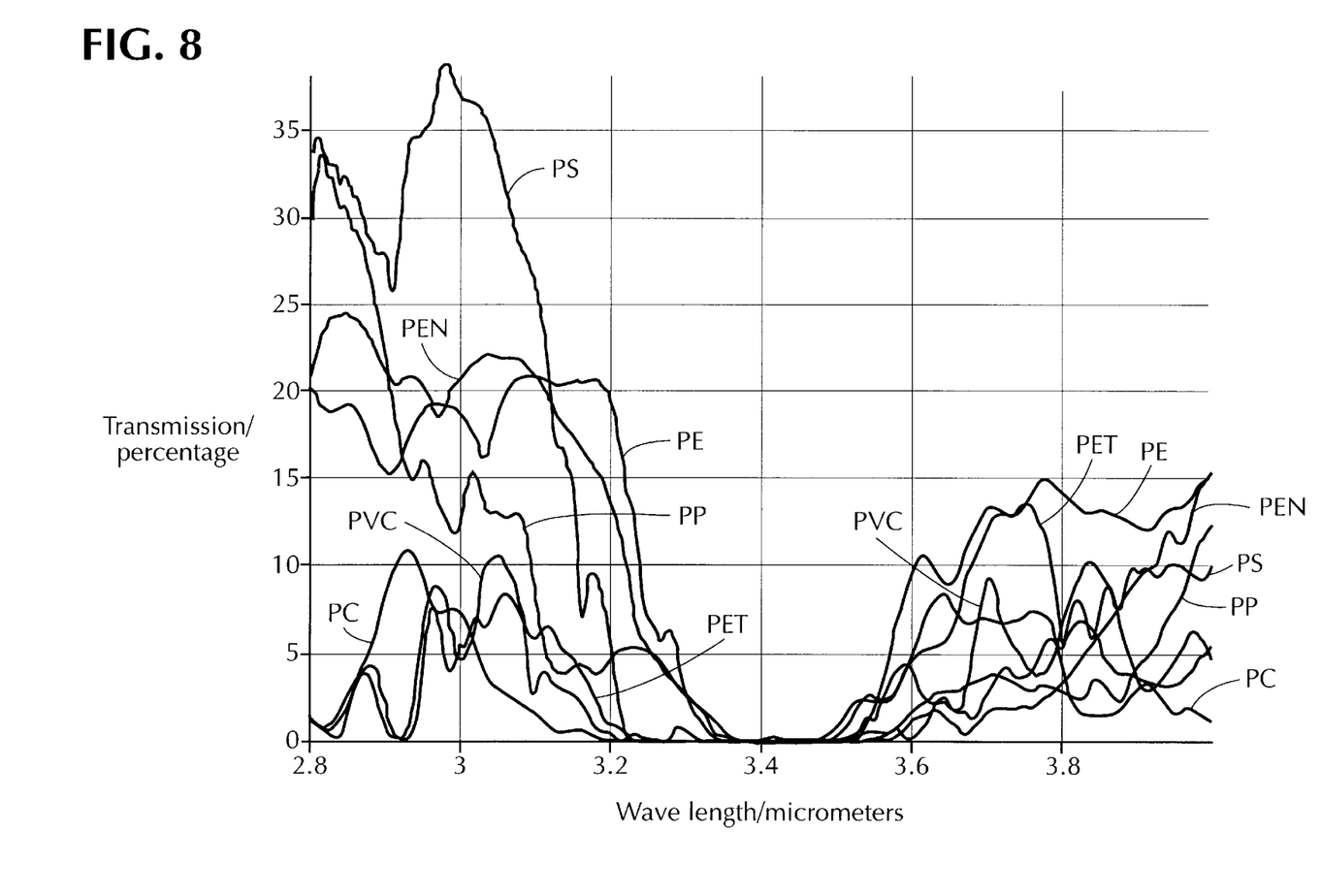
FIG. 8 shows average transmission curves for types of plastics which have been identified in a test installation.

FIG. 8 shows the average transmission curves for each of the types of plastic in question which were identified during the preliminary tests.

According to a prototype of the invention, the envelope filter 14 limited the wavelength range to 2.9–3.8 micrometers. However, it will be appreciated that other wavelength ranges may conceivably be employed by using other filters. The diaphragm 15, which determines how much radiation is to pass through and be sent towards the article, will also ensure that light rays pass through from only one filter at a time. The diaphragm may have a fixed or variable diameter, and an appropriate diameter has been found to be 13 mm, although this must not be perceived as in any way defining the limits of the invention.

In FIG. 2, for the purposes of illustration, it is supposed that the radiation which strikes the article, such as a bottle 20 or 21, is not deflected therein. However, in practice, light rays will be refracted depending on the angle and where on the bottle they fall. However, some of the light rays which pass through the article will always strike the detector 18, optionally via the mirror 19.

In particular when detecting bottles, it would be advantageous to transport these in a horizontal position and concentrate the detection area on the bottle on its neck portion.

A simple amplifier with high and low pass filters may be built into or connected to the detector 18. In a test installation, the signal from the detector was given a sequence of about 170 Hz and thus periodically had a frequency of 170/10 equalling 17 Hz (because of the 10 filters in the filter device 6). For each measurement, 4–5 periods were sampled, whereupon a digital smoothing and normalising was carried out, the signal frequency was computed and the reference point (signal maximum) was localised. FIG. 5 shows the signal as it appeared subsequent to this process.

As previously indicated, the transmission values are computed as the level of the respective signal peak, minus the mean value of two "neighbouring troughs". The computed values are collected in a vector of 10 elements and are compared with corresponding values for a subsequent signal sequence. If the signal varies excessively, the measurement is rejected, but if the signal is acceptable, average values are computed and then passed on to the calibration and identification algorithms.

In FIG. 1 reference numeral 29 indicates peripheral equipment associated with the microprocessor 11, such as equipment for paying a return deposit for articles received, such as returned bottles, and for giving information to a person operating the apparatus if it is a part of a reverse vending machine. The reference numeral 30 indicates yet more peripheral equipment, such as after-treatment equipment in the form of, for instance, sorting devices, compactors, material cutters, additional conveyors etc.

Figure 6:
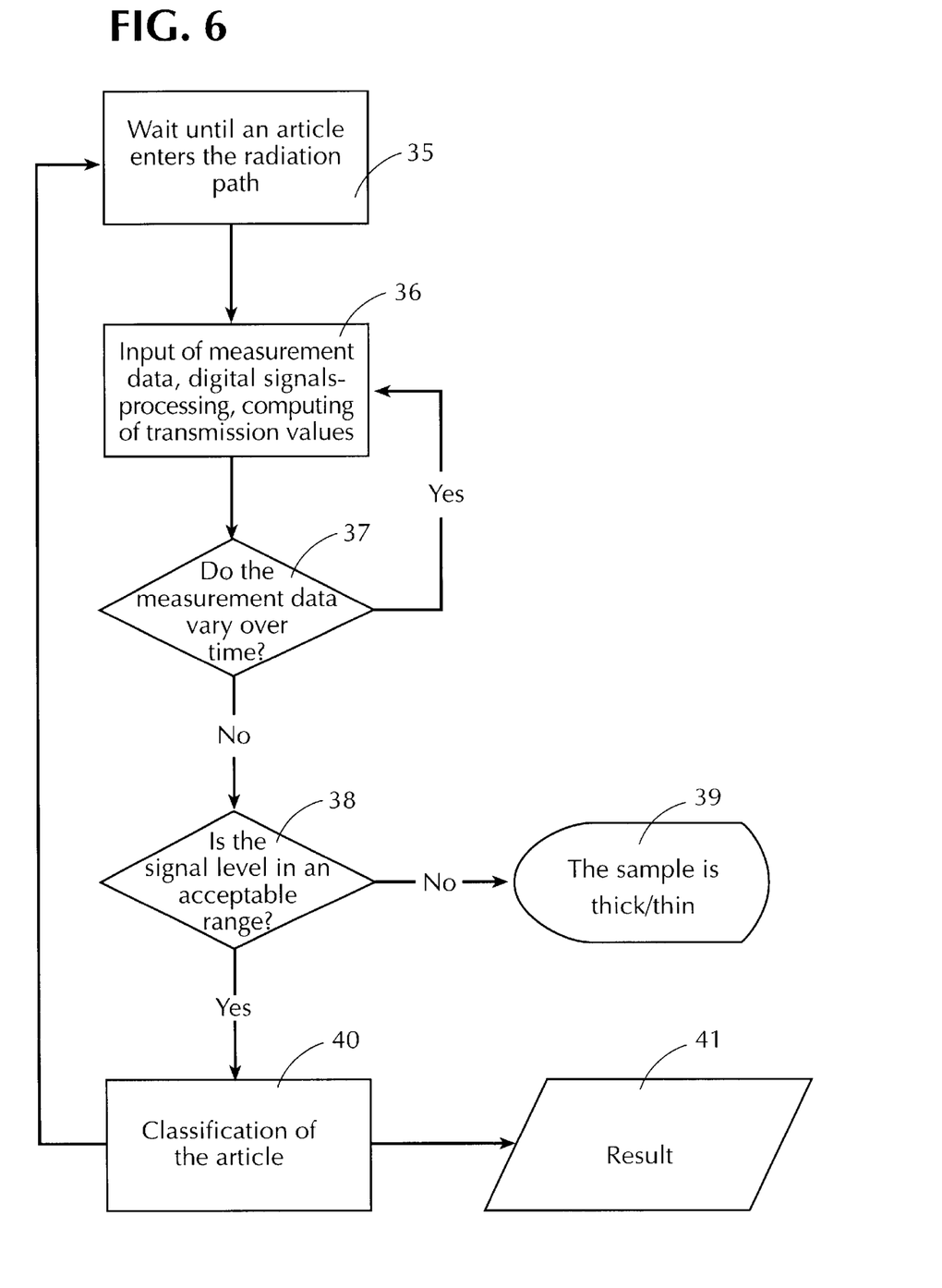
FIG. 6 shows in the form of a flow diagram the series of evaluations which a processor, according to the invention, must make.

In FIG. 6, by way of a summary, the process steps which must be carried out to classify an article entering a detector station are indicated in general terms.

Block 35 indicates that the system is waiting for an article to enter the radiation path. When such an article is present, block 36 indicates that measurement data are fed into the detector 18 with subsequent digital signal processing in the A/D converter 25 and with computation of transmission values with the aid of the microprocessor 11. The decision block 37 indicates that the microprocessor 11 considers whether the sequence of the received and analysed measured values vary over time. If such is the case, measured values must be fed in and processed again. However, if such is not the case, a new decision will be taken as represented by block 38 with respect to whether the signal level is within an acceptable, predetermined range. If this is not the case, as indicated by block 39, e.g., that the article of which a measurement test is taken is too thick or too thin, the measurement will be rejected and the article deemed non-accepted. In such a case, it is possible, via the peripheral equipment as indicated in FIG. 1 by means of reference numeral 34, to convey the article received back to the person who has inserted it, or optionally to convey the article to a receptacle for unidentified articles.

However, if the signal level is in an acceptable range, the article will be classifiable, as indicated at block 40, thus allowing the article to be conveyed to the correct further treatment, whether this be compaction of the article or cutting it up, or to re-use of the article. This is generally indicated by reference numeral 41, which also includes the possibility, via the peripheral equipment 29, of printing out a receipt for the person who inserted the article showing the return deposit value, if any, of the article.

During the testing of a prototype of the apparatus according to the invention, the calibration was done by means of a method which is generally referred to as PLS discriminant analysis, wherein PLS in this connection stands for "Partial Least Squares", and is a method used in the calibration of instruments with many wavelength ranges, and wherein the individual wavelength ranges may be correlated. This type of analysis is well suited for distinguishing between two fractions. One of the fractions can be given a y value of +1, whilst the other fraction can be given a y value of −1, and the PLS analysis can then be used to find an optimal regression vector which distinguishes the two fractions under given conditions. In the case where, e.g., ten filters are used, as shown in FIG. 3, all the computation necessary to find out which fraction an unknown sample belongs to will be to multiply the regression vector by the sequence of measured values which are obtained as the ten filters pass by. In this specific instance, eight regression vectors are computed, wherein the first divides the multidimensional space in two. By examining the decomposition with the aid of an analysis procedure that is known per se, it is seen that PC, PEN and PET constitute one fraction, whilst PE, PP, PS and PVC constitute a second fraction of the typical wavelength range of 2.8–3.9 micrometers. After PC, PEN and PET have been separated as a fraction, a regression vector is computed which separates PEC, one which separates PEN and one which separates PET from this fraction. Similar methodology is used for the other types of plastics.

This method is simple per se and will give satisfactory results, but a drawback of PLS discriminant analysis is that it attempts to plot all articles of one type as the integer 1, whilst all other types are plotted as the integer −1. The regression vector used is therefore not quite optimal, even though the method of analysis is simple. Use of PLS discriminant analysis is therefore only named as a possible method of analysis. Other possible methods of analysis are, e.g., "Principal Component Analysis", direct correlation, Mahalonobis' discrimination, neural network analysis and "fuzzy" logic.

As mentioned above, an article which is to be detected is transported through the detector station in a continuous or discontinuous movement. The discontinuous movement may, e.g., mean that the article, when it comes into the path of the light beam 3, is made to stop briefly once or optionally several times with intervening small movements. If an article, e.g., a bottle, is furnished with large labels, it may be expedient to cause the article to rotate in the detector station until a maximum signal intensity through the reference filter, such as the filter 10' in FIG. 3, is registered. In such a case, it would be of advantage if the article, such as a bottle, were transported in a horizontal position, as indicated by the reference numeral 21, and that in the detector station there is equipment for rotating the article, in the form of peripheral equipment belonging to the block 33.

Figure 9:
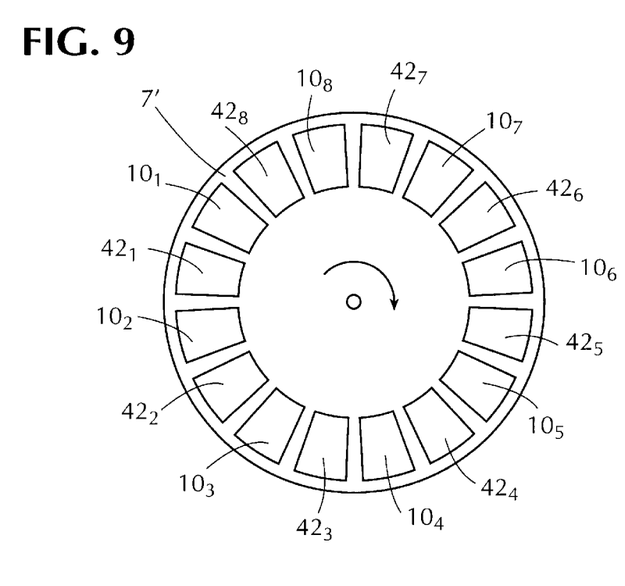
FIG. 9 shows a modification of the filter device in FIG. 3.
Figure 10:
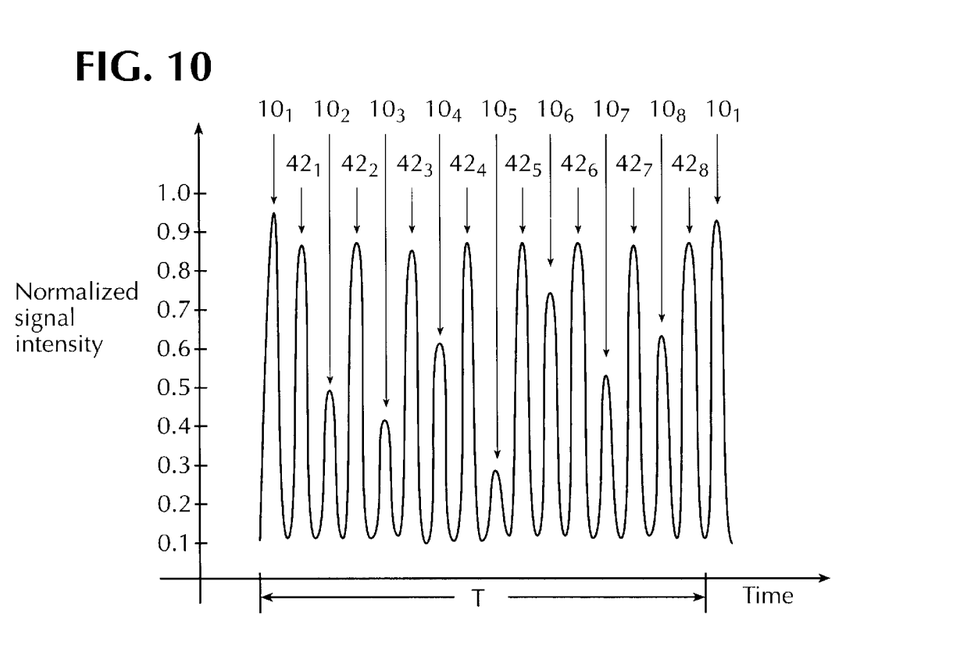
FIG. 10 shows a modification of FIG. 5 by using the filter device of FIG. 9.

In a preferred execution of the invention, the neck of the bottle in particular will be suitable for material detection. FIG. 9 shows a modification of the filter disc 7 which can be seen in FIG. 3. On this FIG. 8 shows a modification of the filter disc 7 which can be seen in FIG. 3. On this chosen version of the filter-carrying disc that does not define the limits of the invention, there is provided a total of eight filters 10, of which the filter $10_1$ is a completely transparent reference filter which preferably, but not necessarily, is made of a diaphragmed but material-free (i.e., open) aperture 16 (see FIG. 2). The other filters $10_2$, $10_3$, $10_4$, $10_5$, $10_6$, $10_7$ and $10_8$ could be selected from among, e.g., the following materials: polycarbonate (PC), polystyrene (PS), polyethylene terephthalate (PET), glass (Pyrex® glass), polyvinyl chloride (PVC), polyethylene (PE), polypropylene (PP) and polyethylene. Between the adjacent filters $10_1$, $10_2$, $10_3$, $10_4$, $10_5$, $10_6$, $10_7$ and $10_8$ there are arranged respective filter-free diaphragms, or diaphragms of the same filter material in all, or diaphragms of limited light area, indicated by $42_1$, $42_2$, $42_3$, $42_4$, $42_5$, $42_6$, $42_7$ and $42_8$, respectively. The diaphragms or apertures 42 will help to produce measured reference values between the measured values of the spectral signatures in the sequence of measured values obtained when light rays successively pass through the filters 10. This will make the determination of such successive measured values more exact because there are always reference values on each side of the signature measured value.

If it is desirable to measure the rotation of the disc 7', the signal obtained via the filter $10_1$ will produce a start reference (greater amplitude than that obtained via the apertures $42_1$, $42_2$, $42_3$, $42_4$, $42_5$, $42_6$, $42_7$ and $42_8$), whilst the diaphragms or apertures 42 will produce subsequent position indication for the subsequent signature measured values and also indicate the rate of rotation of the disc 7' (number of pulses from the diaphragms/apertures 42 per unit of time).

What is claimed is:

1. A method for identifying a material type in an article, including a wholly or partly transparent bottle of plastic or glass, comprising, with the aid of a detector station, irradiating the article with rays from an infrared radiation source, detecting rays which non-absorbed have passed through the article, and then carrying out a correlation analysis of such detected rays, characterised by causing the article to pass through the detector station in a continuous or discontinuous movement;

causing the rays from the radiation source to be successively filtered by filters consisting of wholly or partly transparent materials having different spectral characteristics;

intercepting the rays filtered by the filter and non-absorbed by the article in order to form a sequence of measured values representing characteristic transmission signatures of the article; and     carrying out a correlation analysis of the signatures in relation to statistical models in order to determine the material type of the article.

2. A method as disclosed in claim 1, characterised by causing the filters to move along a circular path.

3. A method as disclosed in claim 1, characterised by at least one of the filters is of a material selected from the group consisting of polyethylene terephthalate, polyethylene naphthalate, polyvinyl chloride, polypropylene, polyethylene, polystyrene, polycarbonate, acrylonitrile-butadiene-styrene copolymer, polymethyl methacrylate, polyamide, polyurethane, polysulphonate, Pyrex® glass, or made as a diaphragmed, material-free aperture.

4. A method a disclosed in claim 1, characterised in that two of the filters are selected to give respectively area-limited light ray penetrability through a diaphragm or aperture to produce a signal peak reference value in the sequence of measured values, and light ray impenetrability to produce a valley reference value in the sequence of measured values.

5. A method as disclosed in claim 1, characterised in that in the sequence of measured values there are produced reference measured values which are adjacent to the respective signature measured values.

6. A method as disclosed in claim 1, characterised by providing a wavelength limitation in the radiation path between the radiation source and the detector.

7. A method as disclosed in claim 1, characterised by providing a partial diaphragming of the rays in the radiation path between the radiation source and the detector.

8. A method as disclosed in claim 1, characterised by deflecting the light rays passing through the article towards the detector by means of a focusing mirror.

9. A method as disclosed in claim 1, characterised by providing in the sequence of measured values at least one reference signal peak caused by area-limited, material-unfiltered light, and     analyzing successively each of the other signal peaks in the sequence of measured values in relation to a mean value of two adjacent signal valleys.

10. A method as disclosed in claim 9, characterised by providing in the sequence of measured values at least one reference signal valley caused by blocking the light rays; and     analyzing each of the other signal valleys in the sequence of measured values in order to form successively said mean value of two adjacent signal values in relation to successive signal peaks.

11. A method as disclosed in claim 9, characterised by computing a light transmission value for an article based on a level value of a respective signal peak minus said mean value.

12. A method as disclosed in claim 11, characterised by collecting the computed light transmission values form a signal cycle in a vector consisting of n elements, wherein n is equal to the number of filters, and comparing them with corresponding values for a subsequent signal period.

13. A method as disclosed in claim 12, characterised by rejecting an article measurement if the difference between two successive signal period values exceeds a threshold within an otherwise acceptable measurement sequence.

14. A method as disclosed in claim 13, characterised by computing the average value of two successive signal period values, and deriving with the aid of a calibration and identification operation, e.g., PLS (Partial Least Squares) discriminant analysis, a unique characterisitic of the material type of which the article is made.

15. A method as disclosed in claim 14, characterised in that the calibration and identification operation includes the use of a calibration and identification algorithm.

16. Use of a method as disclosed in claim 1, in a reverse vending machine for identification and sorting of bottles of different material types.

17. An apparatus for identifying a type of material in an article, including a wholly or partly transparent bottle of plastic or glass, comprising, with the aid of a detector station, irradiating the article with rays from an infrared radiation source, detecting rays which have passed through the article non-absorbed, and then carrying out a correlation analysis of such detected rays, characterised by     a conveyor controlled by a means to cause the article to move continuously or discontinuously and to pass through the detector station;

device in the detector station provided with a plurality of filters consisting of wholly or partly transparent materials having different spectral characteristics to effect successive and different filtration of the rays from the radiation source;

a means arranged to intercept the rays filtered by the filter and non-absorbed by the article in order to form a sequence of measured values representing characteristic transmission signatures of the article; and     an analyzer including a microprocessor, adapted to carry out a correlation analysis of the signatures in relation to statistical models in order to determine the material type of the article.

18. An apparatus as disclosed in claim 17, characterised in that the filters are arranged on a rotatable, round or polygonal disc in order to move along a circular path.

19. An apparatus as disclosed in claim 17, characterised in that the filters are arranged in the wall of a drum which is rotatable about an IR radiation source or the detector, and that the drum has a circular or polygonal cross-section.

20. An apparatus as disclosed in claim 17, characterised in that at least one of the filters is of a material selected from the group consisting of polyethylene terphthalate, polyethylene naphthalate, polyvinyl chloride, polypropylene, polyethylene, polystyrene, acrylonitrile-butadiene-styrene copolymer, polymethyl metharcrylate, polyamide, polyurethane, poly sulphonate, polycarbonate and Pyrex® glass.

21. An apparatus as disclosed in claim 17, characterised in that two of the filters are of an opaque material and in the form of a diaphragmed, but material-free aperture, respectively.

22. An apparatus as disclosed in claim 17, characterised in that an aperture is provided between adjacent filters.

23. An apparatus as disclosed in claim 22, characterised in that each of the diaphragms is made in the form of a diaphragmed aperture or aperture having light-transparent material that is the same for all the apertures.

24. An apparatus as disclosed in claim 17, characterised in that a wavelength limiting envelope filter is provided in the radiation path between the radiation source and the detector.

25. An apparatus as disclosed in claim 24 characterised in that the processor is adapted to compute the average value of two successive signal sequence measured values, and carry out an analysis with the aid of a calibration and identification operation, e.g., PLS (Partial Least Squares) discriminant analysis, in order to give a unique characteristic of the material type of which the article is made.

26. An apparatus as disclosed in claim 17, characterised in that a diaphragm is arranged in the path of a light beam.

27. An apparatus as disclosed in claim 17, characterised in that in association with the detector there is provided a focusing mirror for guiding the light rays which pass through the article to the detector.

28. An apparatus as disclosed in claim 17, characterised in that the processor is adapted to register at least one reference signal peak in the sequence of signature measured values from the detector caused by unfiltered light.

29. An apparatus as disclosed in claim 28, characterised in that the processor is also adapted to register at least one reference signal valley in the sequence of measured values of signals caused by blocking the light rays, and that the processor also has an analyzer for successively analyzing each of the other signal peaks in the sequence of measured values in relation to a mean value.

30. An apparatus as disclosed in claim 29, characterised in that the processor is adapted to compute the light transmission value for an article based on a level value of a respective signal peak minus said mean value of two adjacent signal valleys.

31. An apparatus as disclosed in claim 28, characterised in that the processor is adapted to compute the transmission signature value for an article based on the level of a respective signal peak in relation to the value of an adjacent reference signal peak.

32. A method as disclosed in claim 28, characterised in that the processor is adapted to compute the average value of two successive signal sequence measured values, and carry out an analysis with the aid of a calibration and identification operation, e.g., PLS (Partial Least Squares) discriminant analysis, in order to give a unique characteristic of the material type of which the article is made.

33. An apparatus as disclosed in claim 17, characterised in that the processor is adapted to collect the computed transmission signature measured values from a sequence of measured values in a vector consisting of n elements, wherein n is equal to the number of filters, and compare with corresponding values for a subsequent signal period.

34. An apparatus as disclosed in claim 17, characterised in that the processor is adapted to reject an article measurement if the difference between two successive signal sequence measured values exceeds a threshold.

35. Use of an apparatus as disclosed in claim 17, in a reverse vending machine for identification and sorting of bottles of different material types.

* * * * *